United States Patent [19]

Lacks

[11] Patent Number: 5,434,063
[45] Date of Patent: Jul. 18, 1995

[54] SEQUENTIAL CLONING OF CHROMOSOMES

[75] Inventor: Sanford A. Lacks, Brookhaven, N.Y.

[73] Assignee: The United States of America as represented by the United States Department of Energy, Washington, D.C.

[21] Appl. No.: 811,221

[22] Filed: Dec. 20, 1991

[51] Int. Cl.⁶ .................. C12N 15/10; C12N 15/09
[52] U.S. Cl. .................. 435/172.3; 435/91.1; 435/91.4
[58] Field of Search .............. 435/91.1, 91.4, 91.41, 435/91.42, 172.1, 172.3, 320.1; 536/23.1, 24.2, 24.3

[56] References Cited

U.S. PATENT DOCUMENTS

| | | | |
|---|---|---|---|
| 4,293,652 | 10/1981 | Cohen | 435/172 |
| 4,808,519 | 2/1989 | Hartley et al. | 435/6 |
| 4,808,525 | 2/1989 | McClelland et al. | 435/172.3 |
| 4,863,848 | 9/1989 | Blocker et al. | 435/6 |

OTHER PUBLICATIONS

Mejean, et al., "Rapid Cloning of Specific DNA Fragments of *Streptococcus Pneumoniae* by Vector Integration Into the Chromosome Followed by Endonucleolytic Excision", *Gene*, 15, pp. 289–293, 1981.
Niaudet, et al., "Insertional Mutagenesis in *Bacillus Subtilis:* Mechanisms and Use in Gene Cloning", *Gene*, 19, pp. 277–284, 1982.
Lacks, et al., *Gene*, 104, 11–17 (1991).
Carlson et al. (1982) Cell, vol. 28, pp. 145–154.
Epstein et al. (1986) Journal of Biological Chemistry, vol. 261, pp. 5886–5891.

*Primary Examiner*—Richard A. Schwartz
*Assistant Examiner*—Philip W. Carter
*Attorney, Agent, or Firm*—Daniel D. Park; Thomas G. Anderson; William R. Moser

[57] ABSTRACT

A method for sequential cloning of chromosomal DNA of a target organism is disclosed. A first DNA segment homologous to the chromosomal DNA to be sequentially cloned is isolated. The first segment has a first restriction enzyme site on either side. A first vector product is formed by ligating the homologous segment into a suitably designed vector. The first vector product is circularly integrated into the target organism's chromosomal DNA. The resulting integrated chromosomal DNA segment includes the homologous DNA segment at either end of the integrated vector segment. The integrated chromosomal DNA is cleaved with a second restriction enzyme and ligated to form a vector-containing plasmid, which is replicated in a host organism. The replicated plasmid is then cleaved with the first restriction enzyme. Next, a DNA segment containing the vector and a segment of DNA homologous to a distal portion of the previously isolated DNA segment is isolated. This segment is then ligated to form a plasmid which is replicated within a suitable host. This plasmid is then circularly integrated into the target chromosomal DNA. The chromosomal DNA containing the circularly integrated vector is treated with a third, retrorestriction (class IIS) enzyme. The cleaved DNA is ligated to give a plasmid that is used to transform a host permissive for replication of its vector. The sequential cloning process continues by repeated cycles of circular integration and excision. The excision is carried out alternately with the second and third enzymes.

21 Claims, 8 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 30 base pairs
        ( B ) TYPE: Nucleic Acid
        ( C ) STRANDEDNESS: Double
        ( D ) TOPOLOGY: Linear     ( i i ) MOLECULE TYPE: Genomic (plasmid) DNA     ( i i i ) HYPOTHETICAL: No     ( i v ) ANTI-SENSE: No     ( v i i ) IMMEDIATE SOURCE: Plasmid pLS1

( i x ) FEATURE:
        ( B ) LOCATION: bp 1621-1592

( x ) PUBLICATION INFORMATION:
        ( A ) AUTHORS: Lacks et al.
        ( B ) TITLE: Identification and analysis of
            genes for tetracycline resistance
            and replication functions in the broad-
            host range plasmid pLS1.
        ( C ) JOURNAL: J. Mol. Biol.
        ( D ) VOLUME: 192
        ( F ) PAGES: 753-765
        ( G ) DATE: 1986

( x i ) SEQUENCE DESCRIPTION: SEQ ID NO:1:

```
          TTGATTAAAA CATTTTACCA CATATAAACT                              30
```

( 2 ) INFORMATION FOR SEQ ID NO:2:

( i ) SEQUENCE CHARACTERISTICS:
        ( A ) LENGTH: 23 Base Pairs
        ( B ) TYPE: Nucleic Acid
        ( C ) STRANDEDNESS: Double
        ( D ) TOPOLOGY: Linear     ( i i ) MOLECULE TYPE: Synthetic DNA     ( i i i ) HYPOTHETICAL: No     ( i v ) ANTI-SENSE: No     ( v i ) ORIGINAL SOURCE: Synthesized     ( x i ) SEQUENCE DESCRIPTION: SEQ ID NO:2:

```
             GATCGCATGC GCAGGTGGTT GTC                                  23
```

( 2 ) INFORMATION FOR SEQ ID NO:3:

( i ) SEQUENCE CHARACTERISTICS:
        ( A ) LENGTH: 26 Base Pairs
        ( B ) TYPE: Nucleic Acid
        ( C ) STRANDEDNESS: Double
        ( D ) TOPOLOGY: Linear     ( i i ) MOLECULE TYPE: Synthetic DNA     ( i i i ) HYPOTHETICAL: No     ( i v ) ANTI-SENSE: No     ( v i ) ORIGINAL SOURCE: Synthesized     ( x i ) SEQUENCE DESCRIPTION: SEQ ID NO:3:

-continued

GATCGAATTC GCAGGTTCTT GACATC                                                    26

SEQUENTIAL CLONING OF CHROMOSOMES

The United States Government has rights in this invention pursuant to Contract No. DE-AC02-76CH0016, between the United States Department of Energy and Associated Universities, Inc.

BACKGROUND OF THE INVENTION

1. Field of Invention

This invention relates to a method for the sequential cloning of chromosomal DNA.

2. Background of Related Art

Currently, large sums of money are being spent and great efforts are being made to map the human genome and the genomes of other organisms. Such mapping is of great interest to molecular biologists.

Certain disorders, such as for example, hemophilia and Lou Gehrig's Disease, are associated with defective genetic material. One of the aims of the human genome mapping project is to discover which diseases are associated with defective genetic material. If the structure of such defective genetic material were known, reliable tests could be developed to determine, for example, who would be susceptible to certain forms of cancer, Lou Gehrig's Disease and other genetic disorders.

The circular integration of plasmid DNA into a bacterial chromosome is described by Mejean et al. and by Niaudet et al.; see, Niaudet et al., "Insertional mutagenesis in *Bacillus subtilis*: mechanism and use in gene cloning" *Gene*, 19, 277–284 (1982); and Mejean et al, "Rapid cloning of specific DNA fragments of *Streptococcus pneumoniae* by vector integration into the chromosome followed by endonucleolytic excision" *Gene*, 15, 289–293 (1981). Mejean et al. and Niaudet et al. further disclose that when heterologous DNA in the circularly integrated plasmid have the ability to replicate in a different host bacterium, then a recombinant plasmid may be removed with restriction enzymes, ligated and cloned in that different host bacterium. However, the methods of Mejean et al. and Niaudet et al. are limited to the cloning of specific DNA fragments.

It is a purpose of the invention to provide a method for sequential cloning of genomic DNA.

Another purpose of the present invention is to provide a method for the sequential mapping of a genetic sequence.

Still a further purpose of the present invention is to provide a method to be used in conjunction with the mapping of the human genome.

A method for sequentially synthesizing gene length segments of DNA is described in U.S. Pat. No. 4,293,652. The method includes synthesizing a fragment of double stranded DNA corresponding to a preselected portion of the length of DNA to be synthesized or "cloned". A fragment of the preselected DNA is inserted into the cloning vector. The vector is cloned in an appropriate host. Next, the vector is opened by a restriction enzyme which cuts at the end of the first fragment. Another segment of the preselected DNA is then inserted into the vector. The process is repeated until the entire length of the preselected DNA has been inserted into the vector. The entire length of the preselected DNA may then be cloned by inserting the vector into a suitable host. This method sequentially synthesizes and clones an already known segment of DNA, unlike the method of the present invention, which sequentially clones and maps an unknown segment of DNA.

For a better understanding of the present invention reference is made to the following description, taken together with the accompanying drawings, and its scope will be pointed out in the appended claims.

SUMMARY OF THE INVENTION

The above mentioned and other purposes are achieved by the present invention, which includes a method for the sequential cloning of chromosomal DNA and, also, the chromosomal DNA cloned by this method. The method includes, as an initial step, selecting a target organism having a segment of chromosomal DNA to be sequentially cloned. Next, a short DNA segment homologous to a segment of the chromosomal DNA to be sequentially cloned is isolated. The homologous DNA segment has the first restriction site on either side of the segment. A first vector product is then formed by ligating the homologous segment into a DNA vector which cannot replicate within the target organism. The vector contains, in adjacent or overlapping positions, the first, second, and third restriction sites. The third restriction site is specific for a retrorestriction enzyme (classified as IIS).

The target organism is then transformed with the first vector product. During the transformation process, circular integration of the first vector product into the segment of DNA to be sequentially cloned occurs. The resulting recombinant chromosomal DNA segment includes two homologous DNA segments, one at either end of the inserted vector segment. The resulting recombinant chromosomal DNA is then cleaved with a restriction enzyme specific for the second restriction site to produce a cleaved DNA segment having the second restriction site at each end. The cleaved DNA segment, having the second restriction site at either end, is then circularized by ligation to form the second vector product.

Next, a host organism which is permissive for replication of the vector is transformed with the second vector product, so that the second vector product is selectively replicated. The replicated second vector product is cleaved with the first restriction enzyme and a DNA segment containing the vector and a short segment of DNA homologous to only a portion of the previously isolated DNA segment, which, when ligated, yields a third vector product. The host organism that is permissive for replication of the vector is transformed with the third vector product to facilitate its replication.

The target organism to be sequentially cloned is then transformed with the third vector product, and circular integration of this vector into the chromosomal DNA segment to be cloned is allowed to occur. The resulting recombinant chromosomal DNA segment includes two homologous DNA segments, one at either end of the vector segment. The resulting circularly integrated chromosomal DNA is then cleaved with the retrorestriction enzyme specific for the third restriction site, and the termini of DNA fragments in the digest are rendered blunt-ended by treatment with a suitable agent. The fragments are then circularized by ligation at low DNA concentration to form a fourth vector product. The permissive host is transformed with the fourth vector product to allow its selective replication.

A greater length of the chromosome can be sequentially cloned. This can be accomplished by cleaving the fourth vector product with the restriction enzyme specific for the first restriction site to produce a DNA segment containing the vector and a short segment of DNA that is homologous to a portion of the DNA segment excised with the retrorestriction enzyme. Upon circularization by ligation this becomes the fifth vector product.

Next, the host organism that is permissive for the replication of the vector is transformed with the fifth vector product to facilitate its replication. The organism to be sequentially cloned is then transformed with the fifth vector product, and circular integration is allowed to occur. The chromosomal DNA containing the vector is once again cleaved with the second restriction enzyme, the site for which remains after cleavage with the retrorestriction enzyme in the prior step.

The process may be repeated to sequentially clone further along the length of the chromosome, and under favorable circumstances to sequentially clone the entire length of the chromosome.

An advantage of the present invention is that it can be used to sequentially clone chromosomal DNA without an extensive knowledge of the DNA to be sequentially cloned.

A further advantage of the present invention is that it can be used to sequentially clone entire chromosomes.

A further advantage is that the present invention provides an immediate map of the chromosome in terms of overlapping cloned segments characterized by several restriction sites.

A still further advantage of the present invention is that it provides cloned chromosomal DNA that can be subjected to nucleotide sequence analysis or to genetic modification.

For a better understanding of the present invention reference is made to the following description and figures, the scope of which is pointed out in the appended claims.

DETAILED DESCRIPTION OF THE PRESENT INVENTION

For purposes of understanding the present invention, the following terms are defined:

Homologous DNA—Segments of DNA having the same base sequence.

Non-Homologous DNA—Segments of DNA which do not have the same base sequence.

Walking Along the Chromosome—The extension of cloned DNA from a particular point or segment in the chromosome. The term has been used to describe the screening of a library of random genomic clones by DNA hybridization to find clones overlapping the initially cloned segment, see, Bender et al., "Chromosomal walking and jumping to isolate DNA from the Ace and rosy loci and the bithorax complex in Drosophila melanogaster", *J. Mol Biol.*, 168, 17–33 (1983) In the method of the present invention, however, a vector steps along the chromosome as part of the cloning process itself and overlapping clones are produced. The present invention can be used to extend a region of cloned sequence and, in theory, to sequentially clone an entire genome.

Circular Integration—The sequential cloning approach used in the present invention is based on integration into the chromosome of circular structures composed of DNA segments that are respectively homologous and heterologous to the chromosome. Such integration at various times has been called ectopic integration, see, Stassi et al., "Cloning of chromosomal genes in *Streptococcus pneumoniae*", *Proc. Natl. Acad. Sci. USA*, 78, 7028–7032 (1981); and Mannarelli et al., "Ectopic integration of chromosomal genes in *Streptococcus pneumoniae, J. Bacteriol.*", 160, 867–873 (1984); additive transformation, see, Claverys et al., "Identification of *Streptococcus pneumoniae* mismatch repair genes by an additive transformation approach"*Mol. Gen. Genet.*, 196, 91–96 (1984); and duplicative insertion, see, Morrison et al., "Isolation of transformation-deficient *Streptococcus pneumoniae* mutants defective in control of competence, using insertion-duplication mutagenesis with the erythromycin resistance determinant of pAM$\beta$1", *J Bacteriol.*, 159, 870–876 (1984). Here we shall refer to it as circular integration. Circular integration appears to result from the interaction by circular synapsis of a circular donor molecule with the recipient cell chromosome so that a single-strand crossover integrates the entire circular structure in an additive manner into the chromosome; for a review of this process see Lacks, S. A., "Mechanisms of genetic recombination in gram-positive bacteria", *Genetic Recombination*, Am. Soc. Microbiol., Washington, D.C., p. 43–85 (1988). Prior to integration, the double stranded circular donor molecule is broken within the homologous portion during DNA uptake by the cell and converted to a single stranded donor molecule.

Circular integration only occurs if the circular donor molecule is not able to replicate autonomously in the recipient cell. If the circular donor molecule can replicate within the recipient cell then the circular donor molecule's interaction with the chromosome by circular synapsis, i.e. the pairing of homologous DNA, is merely a transient step that facilitates plasmid establishment, see, Lopez et al., "Facilitation of plasmid transfer in *Streptococcus pneumoniae* by chromosomal homology", J. Bacteriol., 150, 692–701 (1982); and Canosi et al, "Plasmid transformation in *Bacillus subtilis*: effects of insertion of *Bacillus subtilis* DNA into plasmid pC194" *Mol. Gen. Genet.*, 181, 433–440 (1981).

Figure 1:
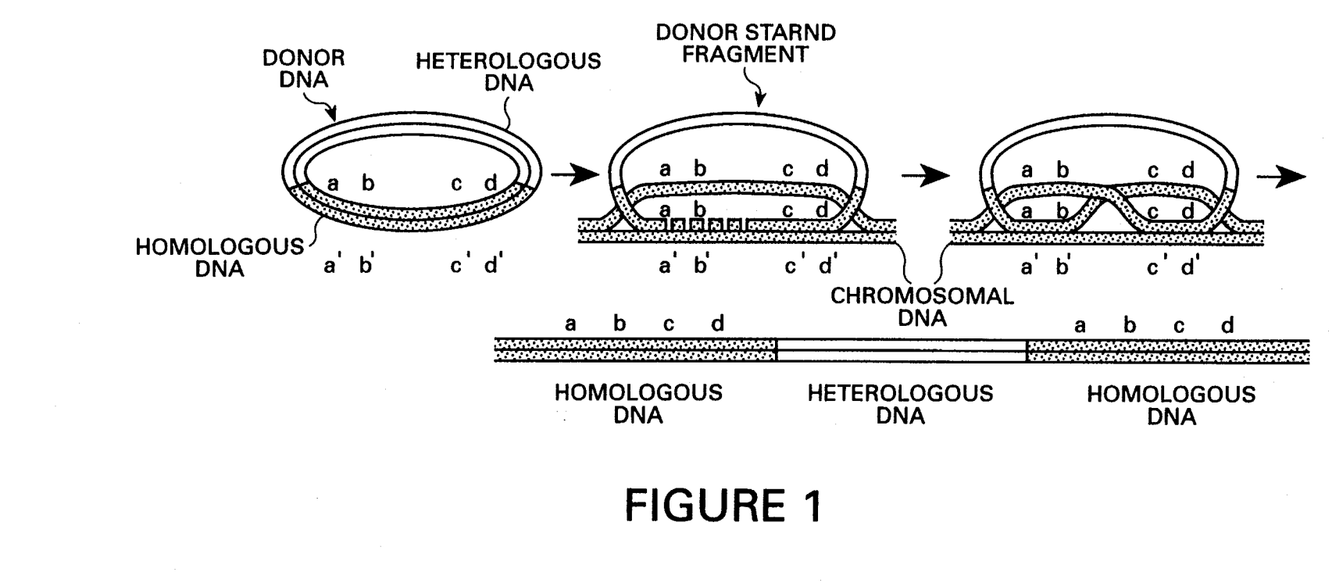
FIG. 1 illustrates the mechanism of circular integration.

Circular integration is illustrated in FIG. 1. A circular double stranded plasmid is created by ligating homologous and non-homologous DNA restriction fragments to form the double stranded circular DNA plasmid illustrated in FIG. 1(a). The plasmid is introduced into the bacterium to be transformed. The plasmid becomes single stranded during the transformation process. Circular synapsis of a single stranded donor fragment occurs at the portion of the chromosome homologous to the donor DNA as illustrated in FIG. 1(b). A single strand crossover integrates the circular donor strand into the chromosome as illustrated in FIG. 1(c).

If the circular DNA structure has no origin of replication suitable for replication in a given host, it cannot replicate within that host. Accordingly, the circular donor DNA remains associated with the chromosome until 1) the donor DNA is degraded or 2) a single-strand recombination event occurs with the chromosomal homolog to the donor DNA, and the donor DNA is inserted into the chromosome by circular integration. In this second situation, called circular integration, replication of the chromosome converts the integrated single strand segment into a duplex form so that the heterologous donor segment is located between duplicated homologous segments. Thus, the product of circular integration contains a direct repeat of the homologous segment flanking the heterologous DNA as is illustrated in FIG. 1(d).

The method of the invention includes the circular integration of a circular DNA vector product into a chromosome. The circular DNA vector product may, for example, contain a plasmid or cosmid vector. The circular vector product is composed of segments of DNA homologous and heterologous to the chromosomal DNA. During circular integration, the circular vector product is broken and the entire vector product is taken into the chromosome of the recipient host bacterium. The heterologous DNA corresponding to the vector is not able to replicate within the recipient bacterium, called a non-permissive bacterium for the vector. The heterologous DNA vector can, however, replicate in a bacterium permissive for replication of the vector, called a permissive bacterium for this vector. The process by which a bacterium takes up plasmids is referred to as transformation.

The sequential cloning method is carried out by circular integration of a vector containing a small segment of DNA homologous to the chromosome followed by excision of a plasmid containing a much larger segment of chromosomal DNA. That recombinant plasmid is subsequently reduced to contain only a small segment of chromosomal DNA located at the other end of the large insert, which is then used for the next circular integration step. The process of the present invention depends on the judicious use of restriction sites in a vector constructed for this purpose. The method should be suitable for sequentially cloning chromosomal DNA in any organism giving adequate frequencies of circular integration. Examples of suitable organisms include the transformable bacteria and yeasts.

The process of the present invention includes the use of a vector (V). The vector (V) must be designed to contain at least three adjacent restriction endonuclease recognition sites, which are not present anywhere else in the vector. The first restriction site (D) must be such that the distance between D restriction sites in the chromosome will be small. Suitable D restriction enzymes include DpnI, Sau3A1, and other endonucleases with 4-bp recognition sites, including those listed in Roberts, "Restriction enzymes and their isoschizomers", *Nucleic Acids Res.*, r271–r313 (1988). Preferably, the distance between D restriction sites will be on the order of 250 bp. The D site will preferably be specific for a 4-bp cutter. The second site (E) is a site which will preferably allow for cloning of large chromosomal DNA fragments. Suitable E restriction site enzymes include EcoRI, SphI, FspI, and other endonucleases with 6-bp recognition sites, including those listed in Roberts, "Restriction enzymes and their isoschizomers" *Nucleic Acids Res.*, 16, r271–r313 (1988). Preferably, E sites will average from 3 kb to 15 kb in length and the E site will be specific for a 6-bp cutter. The third site must cleave the DNA outside of the recognition sequence, so that the adjacent restriction site is preserved. In other words, the restriction enzyme for the F site must have the property of retrorestriction and therefore be a class IIS restriction enzyme. Suitable F site enzymes include BspMI, Tth111II and other class IIS endonucleases found in the listing of Szybalski, et al., "Class-IIS restriction enzymes—a review", *Gene*, 100, 13–26 (1991). The third site is preferably specific for a 6-bp cutter. Most preferably, the E site is also specific for a retrorestriction enzyme.

The vector (V) can replicate autonomously only in the permissive host (P), and not in the nonpermissive host (target) containing the chromosome to be sequentially cloned. The vector must also carry a marker(s) expressible in both hosts to allow selection of transformants. Suitable markers are well known to those skilled in the art and include, for example, genes conferring resistance to certain antibiotics.

Figure 2:
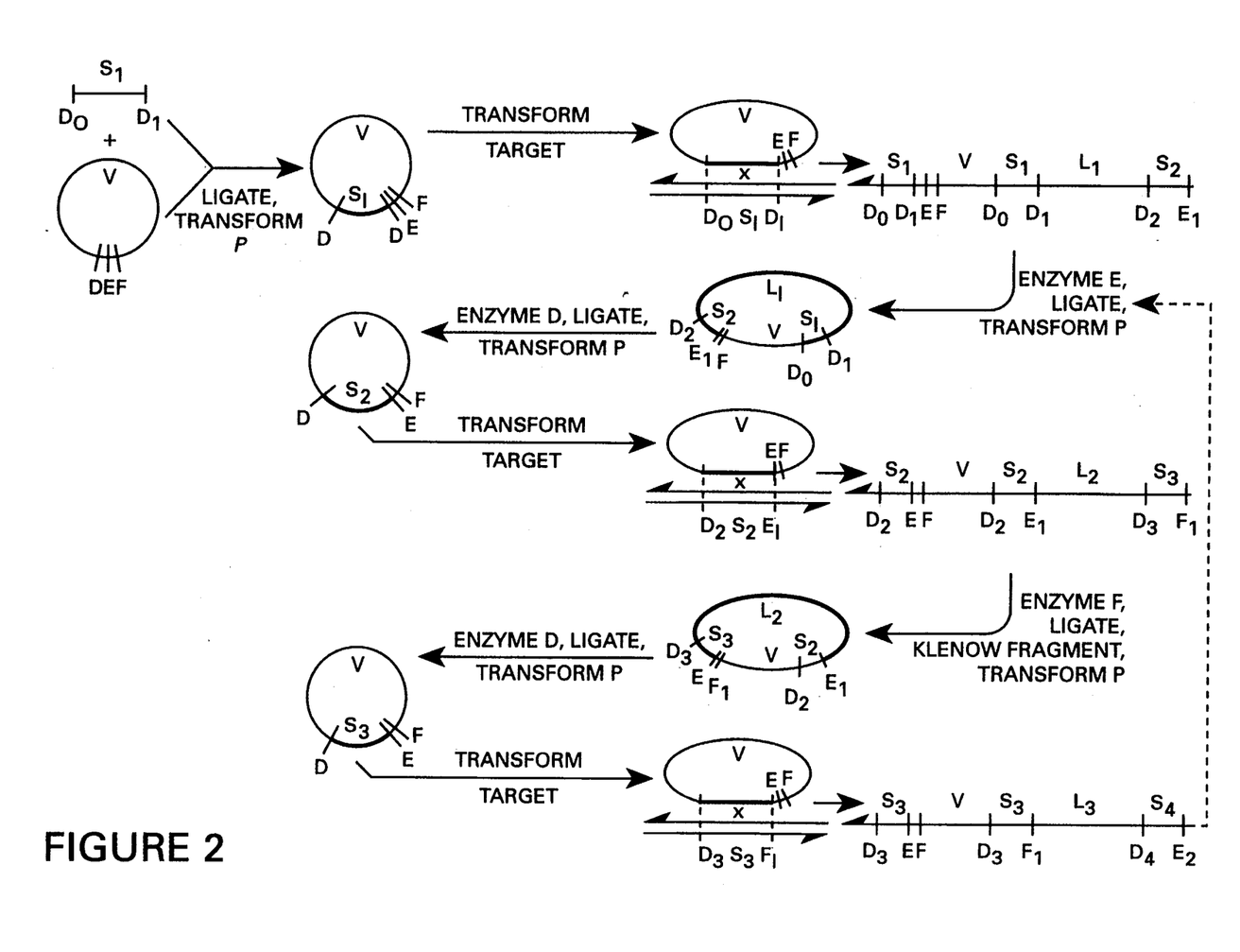
FIG. 2 illustrates a preferred method of the present invention for the sequential cloning of chromosomal DNA.

The process of the present invention begins with the isolation of a fragment of DNA ($S_1$) homologous to a segment of chromosomal DNA. The homologous fragment ($S_1$) is preferably obtained either from a chromosomal segment previously cloned for another purpose or a segment taken randomly from a D enzyme restriction digest of chromosomal DNA. The homologous fragment ($S_1$) is ligated into the D restriction site of the vector to form a circular plasmid (FIGS. 2(a) and (b)). The resulting plasmid is then used to transform the non-permissive target host bacterium. The homologous segment ($S_1$) directs the vector insertion into the chromosome of the target bacterium (FIG. 2(c)). The circular mode of integration results in a duplication of the segment ($S_1$) bracketing the vector (FIG. 2(d)). In other words, the chromosomal DNA of the target bacterium now includes two $S_1$ segments at either end of the inserted vector DNA.

The chromosomal DNA is then treated with restriction enzyme E which cleaves the chromosomal DNA at one end of the inserted vector and at a point further down the chromosome. In other words, the chromosomal DNA is cleaved to produce a segment including the vector DNA (V) and a section of chromosomal DNA ($S_1$, L and $S_2$). The excised DNA is ligated to form the circular plasmid illustrated in FIG. 2(e). The circular plasmid is then used to transform the permissive host bacterium (P) and produce recombinant plasmids in which a substantial segment ($S_1$, $L_1$ and $S_2$) of the target chromosome is cloned. The resulting plasmid can be sequenced and will include the sequence $S_1$-$L_1$-$S_2$.

To walk further down the chromosome, the previous plasmid [FIG. 2(e)] is cut with restriction enzyme D and ligated to form the plasmid illustrated in FIG. 2(f). In general there will be multiple D sites in the cloned E fragment. Such cutting will therefore remove most of the insert and leave only a distal segment between the site closest to the end of the insert at the E site (i.e., $S_1$ and $L_1$ will be excised). Ligation produces a reduced plasmid carrying the $S_2$ fragment illustrated in FIG. 2(f).

The $S_2$ plasmid illustrated in FIG. 2(f) is then used to transform the target bacterium. Transformation of the target bacterium again inserts the vector into the target organism chromosome (by the circular integration mechanism previously described), but further downstream at the site of homology with $S_2$ as illustrated in FIGS. 2(g) and 2(h). The circular integration process results in a duplication of the $S_2$ segment bracketing the vector as shown in FIG. 2(g), i.e. the target organism chromosomal DNA now includes two $S_2$ segments at either end of the inserted vector.

A retrorestriction enzyme (enzyme F) is used to cut out a large fragment of the target chromosome containing the vector. Enzyme F preferably has a 6-bp recognition sequence. Retrorestriction enzyme F cleaves upstream of its recognition sequence in the vector so that the adjacent E site is retained. The use of the retrorestriction enzyme can result in the production of a 5' or 3' overhang. The overhang is treated with an agent to facilitate ligation by producing blunt ends. Suitable agents for 5' overhangs include polymerases such as, for example, the Klenow fragment and T4 DNA polymerase. Suitable agents for 3' overhangs include mung bean nuclease and S1 nuclease.

The restriction enzyme F fragment (F fragment) is ligated to form the circular plasmid illustrated in FIG. 2(i). The F fragment contains a second large target chromosomal fragment which includes chromosomal DNA segments $S_2$, $L_2$ and $S_3$. The F fragment plasmid transforms the permissive host to yield clones of the F fragment. The F fragment plasmid can be sequenced and will include $S_2$-$L_2$-$S_3$.

The F fragment plasmid is treated with restriction enzyme D which removes $S_2$ and $L_2$. $S_2$ and $L_2$ are removed so that the $S_3$ segment can be circularly integrated into the vector. The resulting Enzyme D digestion product is ligated to yield the $S_3$ containing vector illustrated in FIG. 2(j). The $S_3$ containing vector is integrated into the target bacterium chromosome by circular integration of the vector as illustrated in FIGS. 2(k) and 2(l). The circular irtegration process results in a duplication of the $S_3$ segment bracketing the vector (FIG. 2(l)). Therefore, the target organism chromosomal DNA now includes two $S_3$ segments at either end of the inserted vector.

Figure 3:
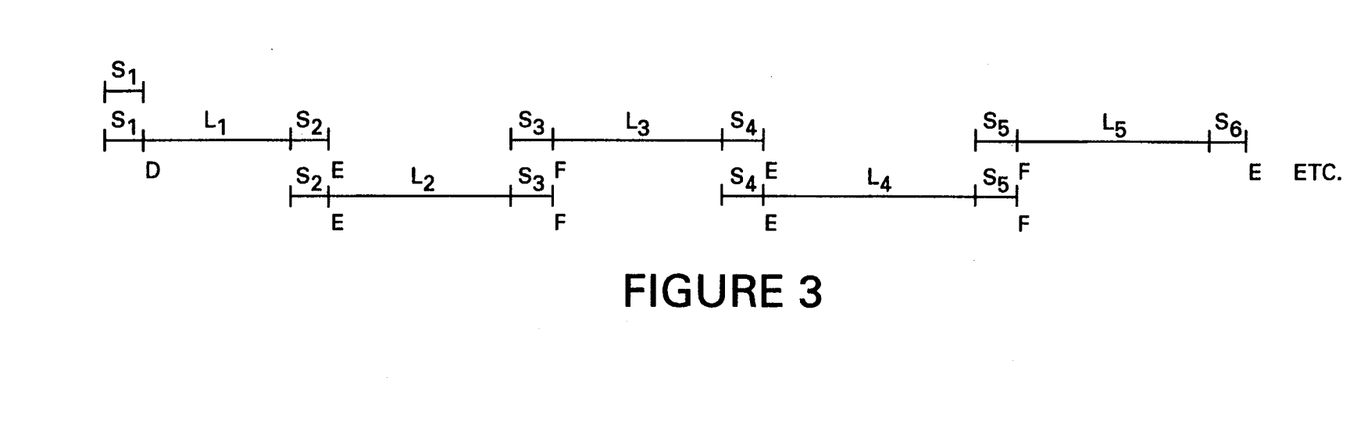
FIG. 3 illustrates overlapping segments of cloned DNA produced by the sequential cloning process illustrated in FIG. 2.

Cutting the circularly integrated chromosomal DNA of FIG. 2(l) with restriction enzyme E is repeated, followed by the other steps, and after the next integration, cutting with restriction enzyme F and subsequent steps are repeated as illustrated in FIG. 2. In this manner alternate segments are cloned down the chromosome as restriction enzyme E and restriction enzyme F fragments. The process of this invention results in the production of successive clones of large chromosomal DNA segments. The homologous DNA of the clones overlap as illustrated in FIG. 3. In FIG. 3, S represents homologous overlapping chromosomal DNA, L represents non-overlapping chromosomal DNA and D, E and F represent cutting sites for different restriction enzymes. The process of the present invention is particularly useful for genome mapping and sequencing.

The present invention does not require knowledge of the chromosomal sequence to be cloned. All that is required to start the process is a segment of DNA having appropriate restriction sites at each end. The fragment can, for example, be produced by treating the chromosomal DNA with an appropriate restriction enzyme.

Figure 9:
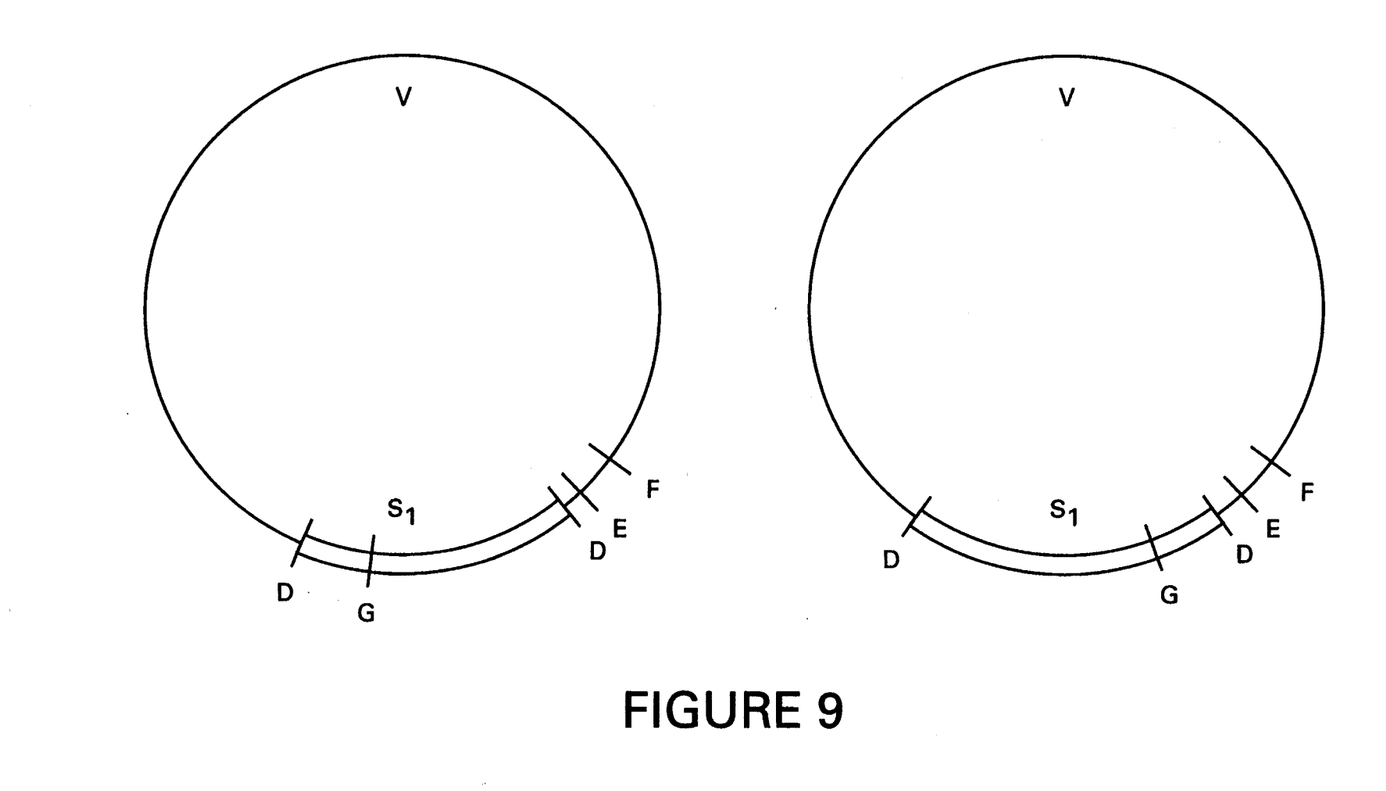
FIG. 9 illustrates vectors for use with the method of the present invention having initial chromosomal segments inserted in opposite orientations.

If the initial chromosomal segment ($S_1$) is originally inserted in the opposite orientation in the vector (see FIG. 9), then sequential cloning will proceed along the chromosome in the opposite direction. In practice, inserts will be obtained in both orientations. The direction of insertion is determined, prior to the start of the sequential cloning process, by cutting with restriction enzymes for D and G, site G is a unique site that is off center in the insert. In one orientation the fragment from E to G is short, in the other orientation, it is long. Since vectors with inserts in opposite orientations will proceed in opposite directions along the chromosome, by starting with one chromosomal fragment the entire chromosome can, in principle, be cloned. Five overlapping clones in one direction are illustrated in FIG. 3. A physical and genetic map of the chromosome can thus be determined, and clones can be sequenced using conventional sequencing techniques. Various considerations which should be taken into account are considered in the following Example.

EXAMPLE 1

Figure 4:
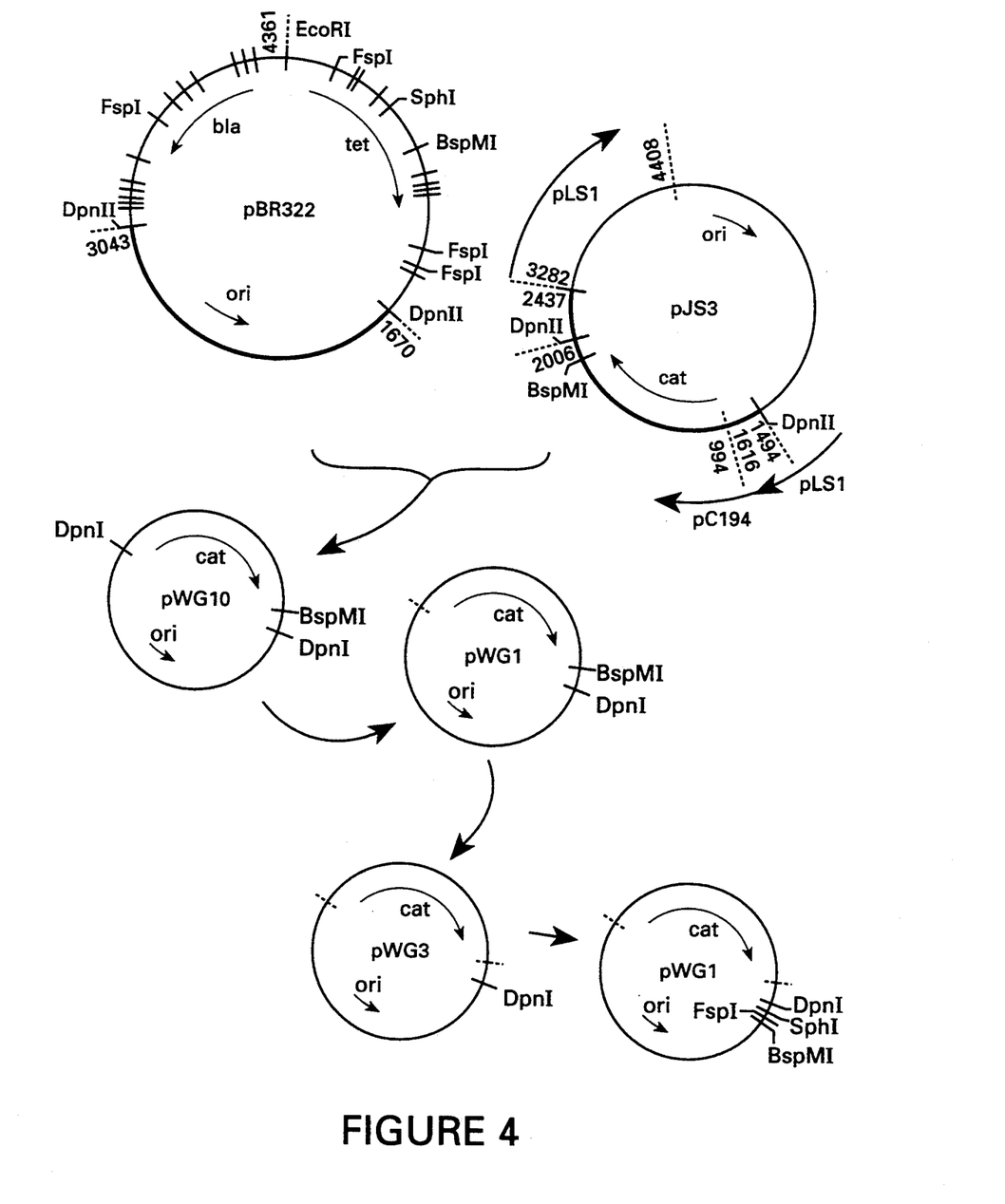
FIG. 4 illustrates the formation of the pWG5 vector.

Seguential Cloning of Part of the S. Pneumoniae Genome Using Vectors That Can Replicate in E. Coli a) Construction of vectors Vectors that can replicate in *E. coli* but not in *S. pneumoniae* and that carry a marker expressed in both species were constructed by combining segments of pBR322 and pJS3 as shown in FIG. 4. Experimental manipulations were carried out according to the suppliers of the restriction enzymes or to Maniatis, et al., *Molecular Cloning, A Laboratory Manual*, Cold Spring Harbor Lab., Cold Spring Harbor, N.Y. (1982). The marker used was the cat gene from the staphylococcal plasmid pC194, the sequence of which is known, see, Horinouchi et al., "Nucleotide sequence and functional map of pC194, a plasmid that specifies inducible chloramphenicol resistance" *J. Bacteriol.*, 150, 815–825 (1982); and which confers $Cm^R$ (chloramphenicol resistance) to both *E. coli*, see, Lacks et al., "Identification and analysis of genes for tetracycline resistance and replication functions in the broad-host-range plasmid pLS1", *J. Mol. Biol.*, 192, 753–765 (1986), and *S. pneumoniae*, see, Ballester et al., "Selective advantage of deletions enhancing chloramphenicol acetyltransferase gene expression in *Streptococcus pneumoniae* plasmids" *Gene*, 41, 153–163 (1986). The source of this marker was a 1.1-kb DpnII fragment of pJS3, which carries an active promoter preceding the cat gene, as reported by Ballester et al., "Selective advantage of deletions enhancing chloramphenicol acetyltransferase gene expression in *Streptococcus pneumoniae* plasmids", *Gene*, 41, 153–163 (1986); and a transcription terminator after it, as reported by de la Campa et al., "Proteins encoded by the DpnII restriction gene cassette: two methylases and an endonuclease", *J. Mol. Biol.*, 196, 457–469 (1987). The *E. coli* replicon was a 1.4-kb fragment, bp 1668 to 3042, described by Balbas et al., "Plasmid vector pBR322 and its special-purpose derivatives—review" *Gene*, 50, 3–40 (1986), of pBR322 grown in *E. coli* strain GM33, which was excised by DpnII. This fragment retains the replication functions, but it lacks the EcoRI and BspMI sites of pBR322 and all DpnII sites except those at its termini. Ligation of the two fragments and transformation of *E. coli* gave pWG10 (see FIG. 4).

Surprisingly, the 1.4-kb DpnII fragment of pBR322 was sufficient to enable replication of the vector plasmid. It had previously been believed that the pBR322 promoter at bp 3124–3096 was necessary for plasmid replication, see, Balbas et al., "Plasmid vector pBR322 and its special-purpose derivatives—a review", *Gene*, 50, 3–40 (1986). Perhaps a sequence in the cat segment of the vector took its place. One possibility is the sequence SEQ ID NO: 1 5′-TTGAtt-18 nucleotides-TAaAcT-3′ at bp 1621–1592 in the pLS1 portion of that segment, see, Lacks et al., "Identification and analysis of genes for tetracycline resistance and replication functions in the broad-host-range plasmid pLS1", *J. Mol. Biol.*, 192, 753–765 (1986); which agrees fairly well (upper case symbols) with the consensus *E. coli* promoter, see, Rosenberg et al , "Regulatory sequences involved in the promotion and termination of RNA transcription", *Ann. Rev. Genet.*, 13, 319–353 (1979).

One DpnI site was removed from pWG10 by partial cleavage with Sau3AI, treatment with S1 nucleate, and ligation to give pWG1 (FIG. 4). Sequence analysis showed that S1 nuclease digestion extended past the overhanging strand at the restriction site. The S1 nuclease digestion resulted in a deletion of bp 3030–3041 in the pBR322 segment and a deletion of the cat segment from bp 1495–1515 (in the pLS1 portion). The single BspMI site in pWG1, which is located in the cat segment but past the end of the cat structural gene, was removed by BspMI cleavage and limited digestion with BAL-31 nuclease. This treatment deleted bp 1954–1982 in the pC194 numbering. The resulting plasmid, pWG3, had only a single DpnI site and no BspMI, EcoRI, FspI or SphI sites.

Figure 5A:
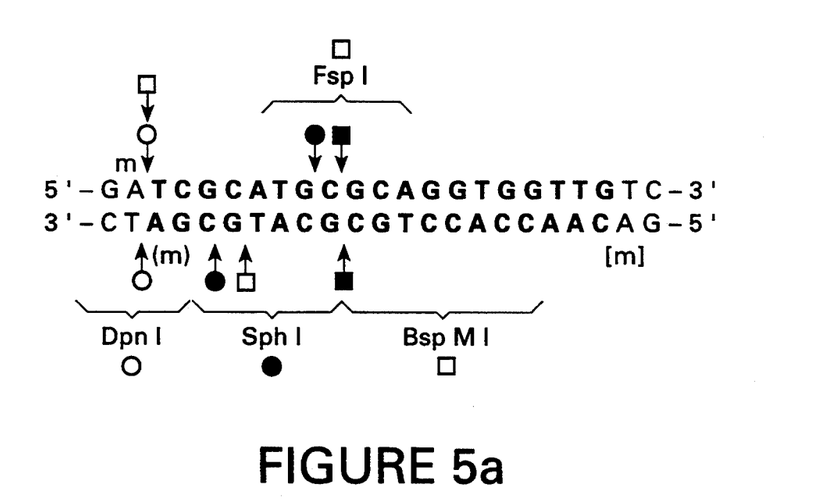
FIG. 5 illustrates two double-stranded oligonucleotides (SEQ ID NO: 2 and SEQ ID NO: 3) that can be used in the formation of vectors. The oligonucleotide illustrated in A was used in the formation of pWG5.
Figure 5B:
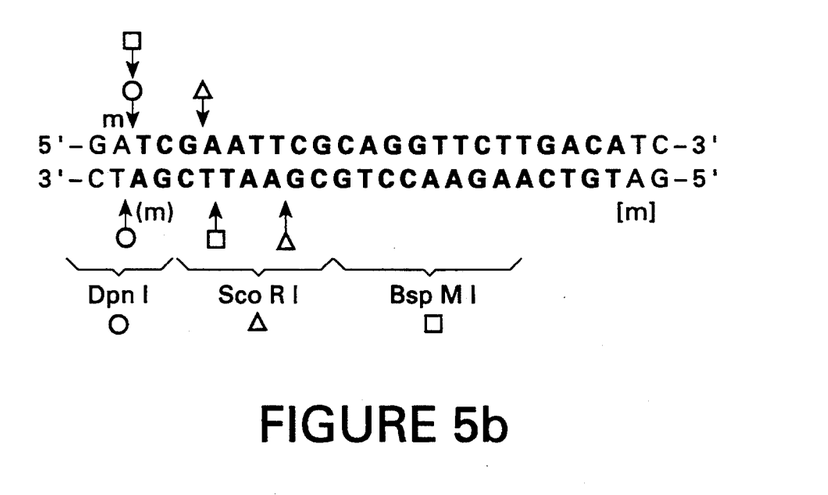

Into the unique DpnI site of pWG3, we inserted the two double-stranded synthetic oligonucleotides SEQ ID NO: 2 and SEQ ID NO: 3 shown boldface in FIG. 5. The oligonucleotide strands were synthesized by the phosphoramidite method on a Systec Microsyn 1450 DNA synthesizer. The insert of FIG. 5B SEQ ID NO: 3 produces the DpnI-EcoRI-BspMI sequence described above. The insert of FIG. 5A SEQ ID NO: 2, which gives the sequence DpnI-SphI-FspI-BSpMI, contains two 6-bp recognition sites restorable after cleavage with BspMI. The advantage of such multiple sites will be discussed below. The plasmid with the DpnI-SphI-FspI-BspMI insert, pWG5, was used to demonstrate sequential cloning.

b) Sequential Cloning of the *S. pneumoniae* genome

Experimental conditions are described in Lacks and Greenberg, "Sequential Cloning by a Vector Walking Along the Chromosome", *Gene*, 104, 11–17 (1991) and references therein. The mal locus of *S. pneumoniae*, which controls utilization of the sugar maltose, was previously mapped genetically, see, Lacks, S., "Genetic regulation of maltosaccharide utilization in pneumococcus", *Genetics*, 60, 685–706 (1968). A 3.5-kb segment containing the malM gene and the start of the following malP gene was cloned and sequenced in pLS70, see, Lacks et al., "Identification of base mismatches recognized by the heteroduplex-DNA-repair system of *Streptococcus pneumoniae*", *Cell*, 31, 327–336 (1982). For a starting point in the *S. pneumoniae* chromosome, a 373-bp Sau3AI fragment from within malM (labeled S1 in FIG. 6) was inserted into pWG5, oriented with its transcriptional polarity the same as cat, to give plasmid pS1. The pS1 plasmid, propagated in *E. coli*, transformed *S. pneumoniae* to yield 6000 $Cm^R$ clones/ml. These clones, as expected, contained no plasmids.

DNA from one clone was digested with SphI, ligated to circularize the fragments, and used to transform *E. coli*. The resulting plasmid (pL1), which was present in all 6 $Cm^R$ transformants that were obtained, contained a pneumococcal chromosomal DNA segment of 1.7 kb. The pL1 plasmid was reduced by digestion with Sau-3AI to contain only a 0.2-kb segment (S2 in FIG. 6).

Subsequent transformation of *S. pneumoniae* with pS2 gave 1600 $Cm^R$ clones/ml. Chromosomal DNA from one clone was digested with BspMI. BspMI produced a 4-base 5′-overhang that was filled in by DNA synthesis using the Klenow fragment of DNA polymerase I, which is also known as PolIk. The BspMI-treated fragment was circularized by ligation and used to transform *E. coli*. Two of three $Cm^R$ transformants contained a plasmid with a 1.3-kb insert, L2. The third appeared to contain pS2, which could have been produced by BspMI excision if the originally integrated pS1 were duplicated as a consequence of the repeated sequences bordering it, see, Vasseghi et al., "Amplification of a chimeric plasmid carrying an erythromycin-resistance determinant introduced into the genome of *Streptococcus pneumoniae*", *Gene*, 21, 285–292 (1983). Plasmid pL2 was reduced by digestion with SauAI to give pS3, a 2.8-kb plasmid. As expected, pS3 retained the SphI site.

Transformation of *S. pneumoniae* with pS3 gave 1000 $Cm^R$ clones/ml. When DNA from one of them was digested with SphI, circularized, and used to transform *E. coli*, 11 $Cm^R$ transformants tested all contained only the original pS3 plasmid. Perhaps the next SphI segment could not be cloned, either because it was too large or because it contained a gene toxic in a high copy number plasmid. However, resort was made to the FspI site in the vector. When the DNA containing integrated pS3 was cut with FspI, circularized, and used to transform *E. coli*, 9 of 15 $Cm^R$ transformants contained pL3, an 8.4-kb plasmid. The remaining 6 $Cm^R$ transformants contained pS3.

c) Restriction mapping of sequentially cloned DNA

Figure 6:
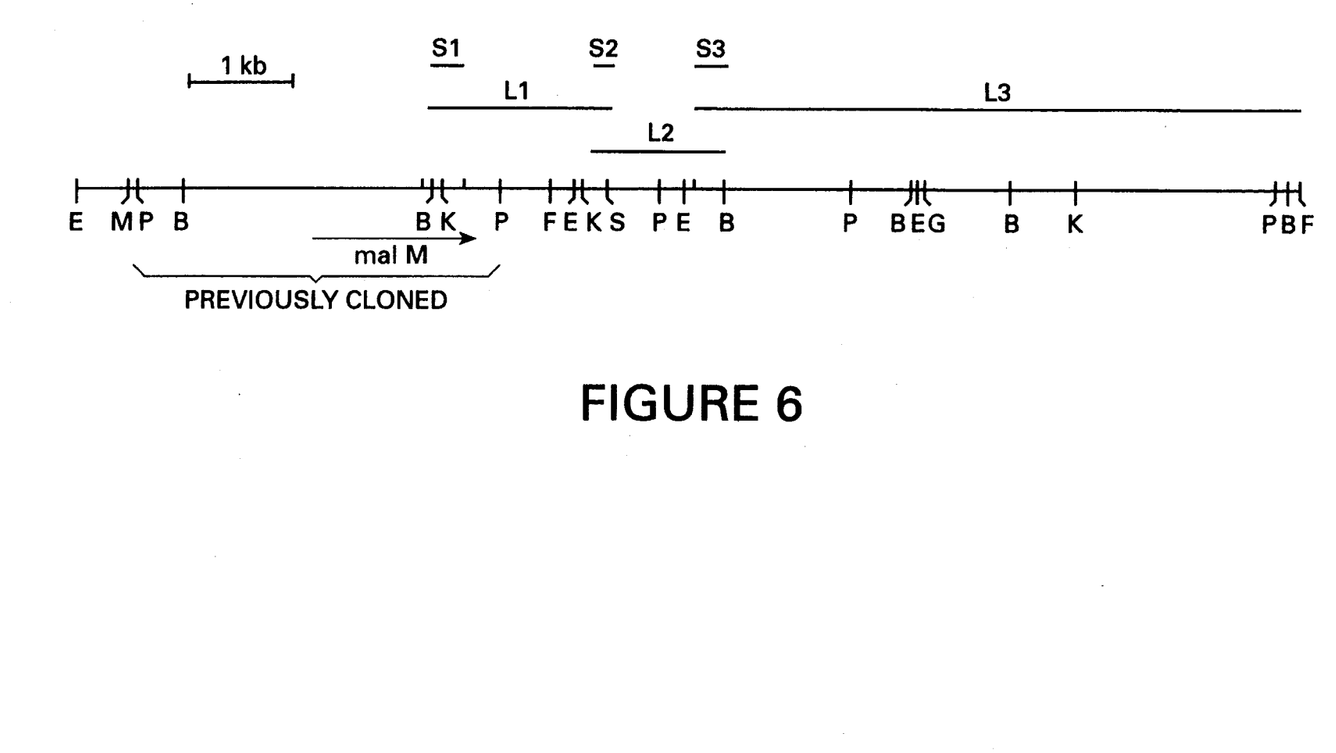
FIG. 6 illustrates a segment of *S. pneumoniae* sequentially cloned using the method of the present invention.

Restriction analysis of pL1, pL2, and pL3 gave the map shown in FIG. 6 for the region downstream from malM. The positions of the S and L segments are indicated on the map. The map is consistent with sequential cloning expectations in that no SphI sites occur within L1, no BspMI sites within L2, and no FspI (or SphI) sites occur within L3.

One step of sequential cloning was taken in the opposite direction with a vector containing an EcoRI site and the S1 segment. In this case the vector contained oligonucleotide B of FIG. 5 (SEQ ID NO: 3), and the S1 segment was oriented in the vector with its transcriptional polarity opposite to cat. Otherwise experimental conditions were similar to the sequential cloning with pWG5. This step extended the mal region map 0.6 kb to the left, as shown in FIG. 6.

d) Confirmation of chromosomal map by Southern blotting

Figure 7:
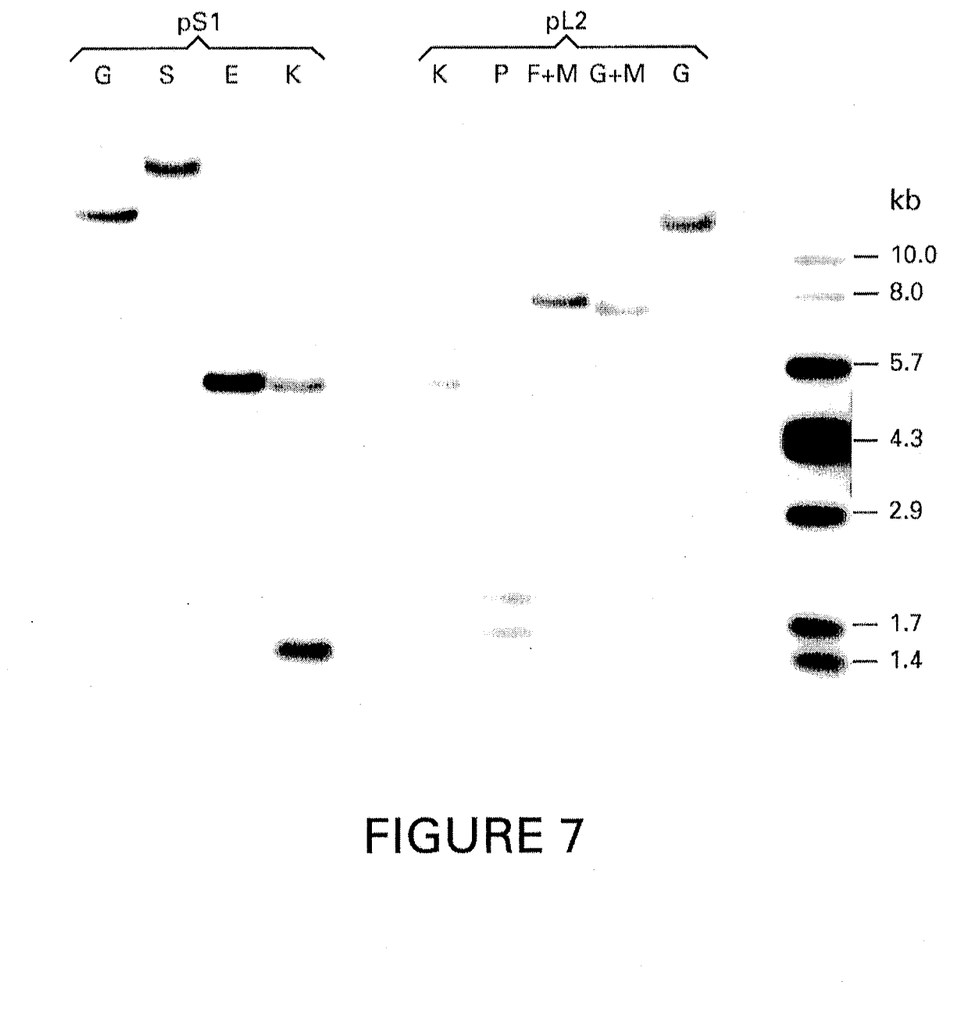
FIG. 7 illustrates a Southern blot confirmation of a partial chromosomal map of *S. pneumoniae* obtained with the present invention.

The accuracy of the sequential cloning procedure was tested by cutting the chromosomal DNA of *S. pneumoniae* with various restriction enzymes and testing for hybridization with probes made from the cloned DNA (pS1 and pL2). Results in FIG. 7 show that pS1 hybridized to a 5-kb EcoRI fragment and to a 1.4-kb KpnI fragment as expected from FIG. 6. The 5-kb KpnI fragment detected by pS1 presumably extends to the left of the KpnI site in malM (FIG. 6). Both pS1 and pL2 hybridized to a BglII fragment of identical size, estimated to be 15 kb. The SphI fragment to which pS1 hybridized is estimated to be approximately 30 kb. For pL2, hybridization with 5-KpnI, 1.5- and 1.8-kb PstI, and 7.5-kb BamHI-BglII fragments corresponded to the restriction map. Only the 7.8-kb FspI fragment to which pL2 hybridized appeared significantly larger than the 7.2-kb expectation. Perhaps a small deletion occurred in the plasmid taken as the pL3 prototype. Inasmuch as the fragments from the chromosome are generally the size predicted from the cloned segments, we conclude that the cloning was indeed sequential according to the scheme outlined in FIG. 8.

e) Further considerations in using the method of the present invention

Figure 8:
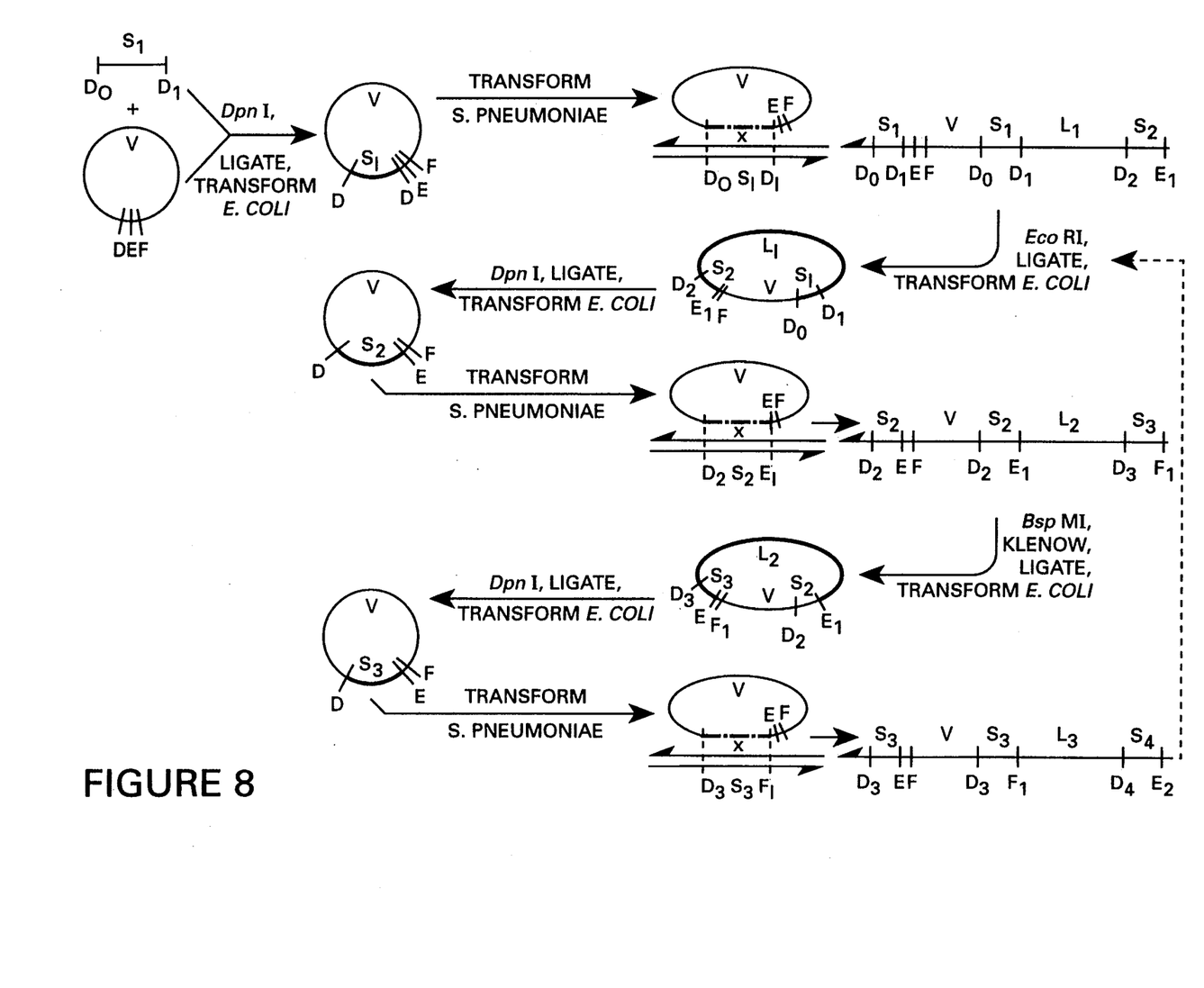
FIG. 8 illustrates the method of the present invention as used for the sequential cloning of part of the *S. pneumoniae* chromosome.

Occasionally, the alternate 6-bp recognition site will occur in the small fragment used for circular integration. For example, in the EcoRI cycle after a BspMI cycle, as depicted in FIG. 8, if an EcoRI site occurs within the small segment ($S_3$), the cloning cannot be extended further. This situation is detectable by the failure to clone a larger fragment. Sequential cloning can be continued, however, by the use of a vector having a different restriction site.

FIG. 4 illustrates a more sophisticated vector, pWG5, having two 6-bp recognition sites, sphI and FspI. The combined limit of which should average 24 cycles. Changing a single G:C bp to C:G in the fourth position from the end of the oligonucleotide shown in FIG. 5A (SEQ ID NO: 2) would produce a Tth111II site, 5'-TGYTTG-3', and the single Tth111II site in the vector (bp 1921-1926 in pBR322) could be eliminated. Since Tth111II, like BspMI, is a retrorestriction enzyme that will cleave in back of the FspI site, these two enzymes could substitute for each other indefinitely. However, since Tth111II gives a 3' overhang, fragments by it will be treated with an agent such as mung bean nuclease, rather than PolIk, to make blunt ends. Thus, as many as 48 cloning cycles might be achieved without interruption.

In other circumstances, a fragment may not be cloned because it is either physically too large or because it contains elements inimical to the host plasmid or cell. Several modifications of the procedure can alleviate such problems. For example, when cloning the genome of a species like *S. pneumoniae* that contains only 40% G+C in its DNA, it would be preferable to use vectors with restriction sites richer in A+T to obtain L segments of smaller average size.

It has been reported that chromosomal DNA fragments from *S. pneumoniae* containing strong promoters are not readily clonable in *E. coli* plasmids, see, Chen, et al., "Cloning of *Streptococcus pneumoniae* DNA fragments in *Escherichia coli* requires vectors protected by strong transcriptional terminators", *Gene*, 55, 179-187 (1987). This problem may, however, be circumvented by the introduction of transcription terminators bracketing the insert in the *E. coli* vector, as reported by Chen et al. (1987) supra.

Furthermore, foreign protein products expressed in *E. coli* may be toxic, particularly when their genes are cloned in high copy number. For this reason it may be preferable to use a low copy vector for sequential cloning. Suitable low copy vectors include pSC101 or pWG5, itself, when grown in an *E. coli* host carrying the pcn mutation.

Another situation that may be encountered in the sequential cloning of bacterial chromosomes is that during the vector integration phase of the cycle, insertion of the vector into the target chromosome could interrupt an essential gene. This would typically occur if the small homologous (S) fragment lay entirely within the gene. This situation can be circumvented by using a larger homologous fragment. The larger fragment could be obtained, for example, by incompletely cleaving the previous L insert with DpnI, so that the S segment is not entirely within the essential gene.

f) Sequential cloning of yeast and mammalian chromosomal DNA

Genetic processes similar to circular integration in bacteria occur in yeast cells after transformation with circularly structured DNA. Although, in this case the interaction apparently occurs between double-stranded donor DNA molecules and the chromosome, as reported by Orr-Weaver and Szostak, "Yeast recombination: the association between double-strand gap repair and crossing-over", *Proc. Natl. Acad. Sci. USA*, 80, 4417-4421 (1983). When a donor molecule that is composed of a vector unable to replicate in yeast joined at both ends to a segment of DNA homologous to the yeast genome transforms the yeast cell, it is circularly integrated into the position of homology in the yeast chromosome, see, Hinnen et al., "Transformation of yeast", *Proc. Natl. Acad. Sci. USA*, 75, 1929-1933 (1978). It is possible, also in yeasts, to subsequently excise a larger fragment of the chromosome and clone it in a host that supports replication of the vector, see, Stiles et al., "DNA sequence of a mutation in the leader region of the yeast iso-1-cytochrome c mRNA", *Cell*, 25, 277-284 (1981). Therefore, the procedure described for sequential cloning of a bacterial genome should be applicable also to yeast chromosomes.

Some difficulties encountered in sequentially cloning bacterial DNA may not be troublesome in yeast. In diploid cells, interruption of one copy of an essential gene may be inconsequential. Differences in protein translation between eukaryotes and prokaryotes may diminish the problem of toxic gene expression in the bacterial host. However, other difficulties may arise that are characteristic of eukaryotic DNA, for example, in extending the cloning through sequences of repetitive DNA.

The sequential cloning approach cannot be directly applied to chromosomes in mammalian cells because DNA that is introduced into mammalian cells is generally inserted indiscriminately into chromosomes rather than integrated at positions of homology, see, Robins et al., "Transforming DNA integrates into the host chromosome", *Cell*, 23, 29-39 (1981). However, large segments (up to 800 kb) of human DNA have been cloned as artificial chromosomes in yeast, see, Little et al., "Yeast artificial chromosomes with 200- to 800-kilobase inserts of human DNA containing HLA, V, 5S, and Xq24-Xq28 sequences", *Proc. Natl. Acad. Sci. USA*, 86, 1598-1602 (1989); and human or other mammalian DNA may be subject to sequential cloning in this form.

While there have been described what are the presently contemplated preferred embodiments of the invention, those skilled in the art will realize that various changes and modifications may be made to the invention without departing from the spirit of the invention, and it is intended to claim all such changes and modifications at falling within the scope of the present invention.

I claim:
1. A method of sequentially cloning chromosomal DNA comprising the steps of:
   (a) forming a first vector product by ligating a first homologous segment which is homologous to a portion of a chromosomal DNA to be sequentially cloned and having a first restriction endonuclease recognition site specific for a first restriction enzyme on each end of said first homologous segment, into a vector having said first restriction endonuclease recognition site, a second restriction endonuclease recognition site, a third restriction endonuclease recognition site, an origin of replication which enables replication of said vector within a permissive host cell and a selectable marker, wherein said first restriction endonuclease recognition site and said third restriction endonuclease recognition site flank said second restriction endonuclease recognition site and wherein said origin of replication and said selectable marker flank an area comprising said first restriction endonuclease recognition site, said second restriction endonuclease recognition site and said third restriction endonuclease recognition site, and wherein said second restriction endonuclease recognition site is specific for a second restriction enzyme and said third restriction endonuclease recognition site is specific for a retrorestriction (class IIS) enzyme;
   (b) transforming a non-permissive target cell which supports circular integration of transforming DNA with said first vector product, wherein said first homologous segment of said first vector product directs circular integration of said first vector product into said chromosomal DNA to be sequentially cloned, at a site at which said first homologous segment is homologous to said chromosomal DNA to be sequentially cloned, and wherein a first recombinant chromosomal DNA segment is formed which includes two of said first homologous segment, one at each end of an integrated vector;
   (c) cleaving said first recombinant chromosomal DNA segment with said second restriction enzyme, wherein a first cleaved chromosomal DNA segment is formed comprising said integrated vector, a first fragment of said chromosomal DNA to be sequentially cloned and two of said second restriction endonuclease recognition site, one at each end of said first cleaved chromosomal DNA segment;
   (d) ligating said first cleaved chromosomal DNA segment to form a second vector product;
   (e) transforming a permissive host cell with said second vector product, wherein a replicated second vector product is expressed;
   (f) cleaving said second vector product with said first restriction enzyme, wherein a second cleaved chromosomal DNA segment is formed comprising said integrated vector and a second homologous segment of chromosomal DNA homologous to a portion of said first recombinant chromosomal DNA segment located in a position distal from said site of the circular integration of said first vector product, and wherein said second homologous segment is of sufficient length to direct circular integration into said chromosomal DNA to be sequentially cloned;
   (g) ligating said second cleaved chromosomal DNA segment to yield a third vector product containing said integrated vector and said second homologous segment of chromosomal DNA;
   (h) transforming a non-permissive host cell with said third vector product, wherein a replicated third vector product is expressed;
   (i) transforming a non-permissive target cell with said third vector product, wherein said second homologous segment of said third vector product directs circular integration of said third vector product into said chromosomal DNA to be sequentially cloned, at a site at which said second homologous segment of said third vector product is homologous to said chromosomal DNA to be sequentially cloned, and wherein a second recombinant chromosomal DNA segment is formed which includes said integrated vector and two of said second homologous segment of said third vector product, one at each end of said integrated vector;
   (j) cleaving said second recombinant chromosomal DNA segment with said retrorestriction enzyme specific for said third restriction endonuclease recognition site, wherein said retrorestriction enzyme leaves the second restriction endonuclease recognition site closest to said third restriction endonuclease recognition site intact to provide a third cleaved chromosomal DNA segment comprising said integrated vector, a second fragment of chromosomal DNA to be sequentially cloned and two of said third restriction endonuclease recognition site, one at each end of said third cleaved chromosomal DNA segment;
   (k) exposing said third cleaved chromosomal DNA segment to an agent that renders nucleic acids blunt-ended, wherein a blunt-ended third cleaved chromosomal DNA segment is formed;
   (l) ligating said blunt-ended third cleaved chromosomal DNA segment to form a fourth vector product; and
   (m) transforming a permissive host cell with said fourth vector product, wherein a replicated fourth vector product is expressed.
2. The method of claim 1 further comprising the steps of:
   (n) cleaving said fourth vector product with said first restriction enzyme, wherein a fourth cleaved chromosomal DNA segment is formed comprising said integrated vector and a third homologous segment of chromosomal DNA homologous to a portion of said second recombinant chromosomal DNA segment located in a position distal from said site of the circular integration of said third vector product, and wherein said third homologous segment is of sufficient length to direct circular integration into said chromosomal DNA to be sequentially cloned;
   (o) ligating said fourth cleaved chromosomal DNA segment to yield a fifth vector product comprising said integrated vector and said third homologous segment of chromosomal DNA;

(p) transforming a permissive host cell with said fifth vector product, wherein a replicated fifth vector product is expressed;

(q) transforming a non-permissive target cell with said fifth vector product, wherein said third homologous segment of said fifth vector product directs circular integration of said fifth vector product into said chromosomal DNA to be sequentially cloned, at a site at which said third homologous segment of said fifth vector product is homologous to said chromosomal DNA to be sequentially cloned, and wherein a third recombinant chromosomal DNA segment is formed which includes said integrated vector and two of said third homologous segment of said fifth vector product, one at each end of said integrated vector; and (r) repeating steps (c) through (m) and (n) through (r) with said third recombinant chromosomal DNA segment, wherein said third recombinant chromosomal DNA segment is substituted for said first recombinant chromosomal DNA segment.

3. The method of claim 1, wherein said first homologous segment is a segment isolated from said chromosomal DNA to be sequentially cloned by cleavage with said first restriction enzyme.

4. The method of claim 1 wherein said vector is selected from the group consisting of plasmid vectors and cosmid vectors.

5. The method of claim 1, wherein said second restriction endonuclease recognition site is specific for a retrorestriction enzyme.

6. The method of claim 1, wherein said agent that renders nucleic acids blunt-ended is selected from the group consisting of PolIk, T4 DNA polymerase, mung bean nuclease and S1 nuclease.

7. The method of claim 1, wherein said vector is a low-copy number vector.

8. The method of claim 7, wherein said low-copy number vector is pSC101.

9. The method of claim 1, wherein said permissive host cell further includes a mutation which reduces the number of replicated vector products being expressed.

10. The method of claim 1, wherein said non-permissive target cell includes a segment of mammalian 11. The method of claim 10, wherein said mammalian DNA comprises a segment of human DNA.

12. The method of claim 1, wherein said non-permissive target cell is selected from the group consisting of yeast cells and bacteria cells.

13. The method of claim 1 further comprising:
transforming a permissive host cell with said first vector product, wherein a replicated first vector product is expressed; and
cleaving said replicated first vector product with a fourth restriction enzyme specific for a fourth restriction endonuclease recognition site, said fourth restriction endonuclease recognition site is located off-center in said first homologous segment, and with said first restriction enzyme specific for said first restriction endonuclease recognition site, wherein an insertion orientation of said first homologous segment is determined.

14. The method of claim 13, wherein said fourth restriction enzyme is a 6-bp cutter other than the restriction enzyme being utilized as said second restriction enzyme.

15. The method of claim 14, wherein said second restriction enzyme is SphI and said fourth restriction enzyme is FspI.

16. The method of claim 1, wherein said vector further comprises transcription terminators bracketing said area of said vector comprising said first restriction endonuclease recognition site, said second restriction endonuclease recognition site and said third restriction endonuclease recognition site.

17. The method of claim 1, wherein said first restriction endonuclease recognition site is specific for a 4-bp cutter restriction enzyme.

18. The method of claim 17, wherein said 4-bp cutter restriction enzyme is selected from the group consisting of DpnI and Sau3AI.

19. The method of claim 1, wherein said second restriction endonuclease recognition site is specific for a 6-bp cutter restriction enzyme.

20. The method of claim 19, wherein said 6-bp cutter restriction enzyme is selected from the group consisting of EcoRI, SphI and FspI.

21. The method of claim 1, wherein said third restriction endonuclease recognition site is specific for said retrorestriction (class IIS) enzyme selected from the group consisting of BspMI and Tth111II.

* * * * *